United States Patent [19]

Tanaka et al.

[11] 4,083,996
[45] Apr. 11, 1978

[54] NOVEL HYDROXAMIC ACID DERIVATIVES AND MEDICAMENTS FOR TREATMENT OF UROLITHIASIS AND PYELONEPHROSIS COMPRISING SUCH DERIVATIVES

[75] Inventors: Satoru Tanaka, Higashi-kurume; Keiichi Munakata, Yono, both of Japan

[73] Assignee: Eisai Co., Ltd., Tokyo, Japan

[21] Appl. No.: 769,847

[22] Filed: Feb. 17, 1977

[30] Foreign Application Priority Data

Feb. 20, 1976 Japan ............................ 51-16988
Jun. 10, 1976 Japan ............................ 51-67077
Jun. 10, 1976 Japan ............................ 51-67078

[51] Int. Cl.$^2$ ..................... A61K 31/185; C07C 83/10
[52] U.S. Cl. ............................ 424/315; 260/295 AM; 260/332.2 C; 260/340.9 R; 260/347.3; 260/500.5 H; 424/263; 424/275; 424/282; 424/285
[58] Field of Search ................. 260/500.5 H; 424/315

[56] References Cited

U.S. PATENT DOCUMENTS 3,728,380   4/1973   Johnson et al. ............... 260/500.5 H

OTHER PUBLICATIONS

Wald et al., "Chemistry and Industry", Jan. 14, 1967, pp. 71–73.
Buraczewski et al., "Bulletin de l'Academie Polonaise des Sciences", Serie des Sciences Chimiques, vol. XII, No. 14, 1964, pp. 773–779.

*Primary Examiner*—Joseph E. Evans
*Attorney, Agent, or Firm*—Wenderoth, Lind & Ponack

[57] ABSTRACT

A novel compound having the general formula:

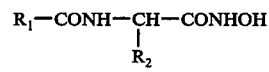

wherein $R_1$ is a residual group selected from the group consisting of substituted phenyl, carbonoylaminophenyl and heterocyclic groups, and $R_2$ is hydrogen or methyl group, and its salts of a pharmacologically acceptable base and a novel medicament containing the compound or its salt mentioned above as a principal component; and the compound and the salt thereof having superior effect for the treatment of urolithiasis and the pyelonephrosis by exhibiting a strong urease inhibitory action, a high transfer rate into the urine and a low toxicity.

7 Claims, No Drawings

NOVEL HYDROXAMIC ACID DERIVATIVES AND MEDICAMENTS FOR TREATMENT OF UROLITHIASIS AND PYELONEPHROSIS COMPRISING SUCH DERIVATIVES

This invention relates to novel hydroxamic acid derivative having the general formula:

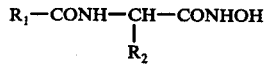

wherein $R_1$ is a residual group selected from the group consisting of a substituted phenyl group represented by a formula:

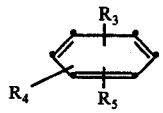

wherein $R_3$, $R_4$ and $R_5$ are selected from the group consisting of hydrogen and a lower alkoxy group, provided that at least one of them is a lower alkoxy group, and two of them may be linked each other to form an alkylene dioxy group; a carbonylaminophenyl group represented by a formula:

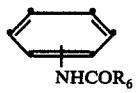

wherein $R_6$ is a lower alkyl group; and
a heterocyclic residue selected from the group consisting of furan, thiophene and pyridine, and $R_2$ is hydrogen or methyl group, provided that when $R_1$ is carbonylaminophenyl group, $R_2$ is hydrogen, and its salt of a pharmacologically acceptable base, as well as medicaments for the urolithiasis and the pyelonephrosis due to the infection of the urease-producing bacterium, which contain said derivative or salt as a principal component.

Said derivative represented by the general formula I is synthesized, for example, according to the following reaction schema:

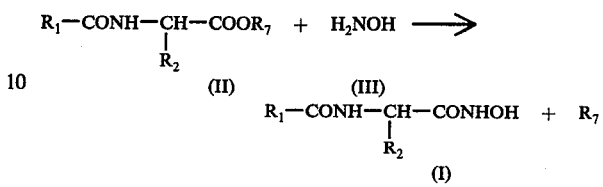

wherein $R_1$ and $R_2$ represent the same meanings as defined above, and $R_7$ represents a lower alkyl radical. More particularly, the compound (I) is obtained by reacting a lower alkyl ester of 2-(substituted benzamide) acetic acid or an alkyl ester of N-(heterocyclic carbonyl)-glycine represented by the general formula (II) with hydroxylamine (III).

The reaction is generally carried out in a lower alcoholic solvent as a reaction medium, for example, methanol, ethanol, propanol, iso-propanol and the like. This reaction is usually carried out in the presence of an alkaline reagent which may be exemplified by an alkali hydroxide, such as sodium hydroxide, potassium hydroxide and the like, and an alkaline bicarbonates such as sodium bicarbonate, potassium bicarbonate and the like.

When the reaction product is diffucult to crystallize and, therefore, difficult to isolate, there may be employed for example a method which comprises once forming a chelate of the product with cupric chloride, copper acetate, copper sulfate and the like, followed by decomposing said chelate, and isolating the reaction product.

Typical compounds represented by the general formula (I) are exemplified in the following Table 1.

Table 1

Compounds represented by the formula I

| Compound | $R_1$ | $R_2$ | Molecular formula Melting point (° C.) | Elementary Analysis Calculated (%) Found (%) | | |
|---|---|---|---|---|---|---|
| | | | | C | H | N |
| A | CH₃O—⌬— | H | $C_{10}H_{12}N_2O_4$ | 53.57 | 5.39 | 12.50 |
| | | | 161.0 – 161.5 | 53.56 | 5.39 | 12.61 |
| B | CH₃O—⌬— | H | $C_{10}H_{12}N_2O_4$ | 53.57 | 5.39 | 12.50 |
| | | | 132.0 – 132.5 | 53.53 | 5.42 | 12.70 |
| C* | CH₃O—⌬— | CH₃ | $C_{11}H_{14}N_2O_4$ | 55.45 | 5.92 | 11.76 |
| | | | 151.0 – 152.0 | 55.42 | 6.00 | 12.00 |

Table 1-continued

Compounds represented by the formula I

| Compound | $R_1$ | $R_2$ | Molecular formula / Melting point (° C.) | Elementary Analysis Calculated (%) / Found (%) | | |
|---|---|---|---|---|---|---|
| | | | | C | H | N |
| D | 2-methoxyphenyl | H | $C_{10}H_{14}N_2O_4$ | 53.57 | 5.39 | 12.50 |
| | | | 177.0 – 177.5 | 53.45 | 5.37 | 12.61 |
| E | 4-ethoxyphenyl ($H_5C_2O$–) | H | $C_{11}H_{14}N_2O_4$ | 55.45 | 5.92 | 11.76 |
| | | | 137.5 – 138.5 | 55.43 | 5.97 | 11.67 |
| F | 4-n-propoxyphenyl (n-$H_7C_3O$–) | H | $C_{12}H_{16}N_2O_4$ | 57.13 | 6.39 | 11.11 |
| | | | 150.0 – 151.0 | 57.23 | 6.48 | 11.21 |
| G | 4-n-butoxyphenyl (n-$H_9C_4O$–) | H | $C_{13}H_{18}N_2O_4 \cdot$ 1/3$H_2O$ | 57.34 | 6.91 | 10.28 |
| | | | 126.0 – 127.0 | 57.59 | 6.61 | 9.80 |
| H | 3,4-methylenedioxyphenyl | H | $C_{10}H_{10}N_2O_5$ | 50.42 | 4.23 | 11.76 |
| | | | 156.0 – 157.0 | 50.27 | 4.33 | 11.69 |
| I | 2,3-dimethoxyphenyl | H | $C_{11}H_{14}N_2O_5$ | 51.96 | 5.55 | 11.02 |
| | | | 139.0 – 139.5 | 51.84 | 5.61 | 11.13 |
| J | 3,4,5-trimethoxyphenyl | H | $C_{12}H_{16}N_2O_6$ | 50.70 | 5.67 | 9.86 |
| | | | 154.5 – 155.5 | 50.67 | 5.70 | 9.99 |
| K | 2,3,4-trimethoxyphenyl | H | $C_{12}H_{16}N_2O_6$ | 50.70 | 5.67 | 9.86 |
| | | | 133.5 – 134.5 | 50.37 | 5.92 | 9.46 |
| L* | 3-methoxyphenyl | $CH_3$ | $C_{11}H_{14}N_2O_4$ | 55.45 | 5.92 | 11.76 |
| | | | 152.0 – 153.0 | 55.39 | 6.03 | 11.92 |
| M | 4-acetamidophenyl (NHCOCH$_3$) | H | $C_{11}H_{13}N_3O_4$ | 52.58 | 5.22 | 16.73 |
| | | | 178.0 – 179.0 | 52.40 | 5.37 | 16.63 |

Table 1-continued

Compounds represented by the formula I

| Compound | R₁ | R₂ | Molecular formula Melting point (° C.) | Elementary Analysis Calculated (%) / Found (%) | | |
|---|---|---|---|---|---|---|
| | | | | C | H | N |
| N | H₃COCHN—⟨phenyl⟩— | H | $C_{11}H_{13}N_3O_4$ | 52.58 | 5.22 | 16.73 |
| | | | >200** | 52.37 | 5.27 | 16.75 |
| O | ⟨phenyl⟩—, NHCOCH₂CH₃ | H | $C_{12}H_{15}O_4N_3$ | 54.33 | 5.70 | 15.84 |
| | | | 158.5 – 159.5 | 54.14 | 5.72 | 15.80 |
| P | H₃CH₂COCHN—⟨phenyl⟩— | H | $C_{12}H_{15}O_4N_3$ | 54.33 | 5.70 | 15.84 |
| | | | >205** | 54.07 | 5.74 | 15.88 |
| Q | ⟨phenyl⟩—, NHCOCH₂CH₂CH₃ | H | $C_{13}H_{17}O_4N_3$ | 55.90 | 6.14 | 15.05 |
| | | | 158.0 – 159.0 | 55.71 | 6.13 | 15.10 |
| R | ⟨furan⟩— | H | $C_7H_8N_2O_4$ | 45.65 | 4.38 | 15.21 |
| | | | 150.0 – 151.0 | 45.85 | 4.46 | 15.01 |
| S | ⟨thiophene⟩— | H | $C_7H_8N_2SO_3$ | 41.99 | 4.03 | 13.99 |
| | | | 153.0 – 153.5 | 41.89 | 4.02 | 14.25 |
| T | ⟨pyridine⟩— | H | $C_8H_9N_3O_3$ | 49.23 | 4.65 | 21.53 |
| | | | 249.0 – 251.0 | 49.00 | 4.68 | 21.71 |
| U* | ⟨thiophene⟩— | CH₃ | $C_8H_{10}N_2SO_3$ | 44.85 | 4.71 | 13.07 |
| | | | 159.0 – 160.0 | 44.90 | 4.80 | 13.16 |

*Racemate or racemic modification
**Decomposition point

The salts of the compound represented by the general formula (I) with pharmacologically acceptable bases can be exemplified by salts of inorganic bases, for example, the salts of sodium, potassium, magnesium, aluminium and the like, and salts of organic bases, for example, the salts of piperidine, morpholine, dimethylamine, diethylamine and the like.

The urolithiasis is one of incurable diseases in a recent urinary area, wherein the urolithiasis is referred to a general term of diseases of renal, ureteral, vesical, urethral, prostatic calculus and the like.

The urolithiasis is classified broadly, in accordance with an origin of the calculus, into a phosphate, an oxalate and a ureate calculus diseases and the like. It is often affirmed clinically that they are in a state of a mixed or complex calculus.

The percentage of the phosphate calculus disease in all calculus diseases is assumed to be 40–60% inclusive of the mixed calculus from various statistic data, on the basis of all patients.

The phosphate calculus is generally formed according to the following steps:

Urea in the urine is decomposed into ammonia by a urease-producing bacterium such as Bacillus proteus infected to the urinary tract; the urine is then alkalized by said ammonia, resulting in deposition of the calculus as an insoluble phosphate.

One of clinical countermeasure for the phosphate calculus disease at the present time is to remove the caclulus by means of surgical treatment, and the other is to remove the urease-producing bacterium such as Bacillus proteus by an antibiotics for the urinary tract system such as Ampicillin and the like. However, there are many cases to be unable to recover by undergoing surgical treatment, because the phosphate calculus disease often repeats recurrences. The effect of the antibiotics for the urinary tract to the Bacillus proteus and the like is not also sufficient, and the administration for a long period of time is not preferable in viewpoint of byeffects. For such reasons, the third treatment has been desired clinically.

As one of the third treatment, there has been also studied a treatment which comprises administering a urease inhibitor, in order to firstly inhibit the activity of urease per se, and to secondarily prevent the generation of ammonia.

It has been reported that many hydroxamic acid compounds generally exhibit the particular urease inhibitory action. However, the hydroxamic acid compounds can generally not be easily transferred to the urine in a form having a urease inhibitory action, since their metabolism in the body is rapidly proceeded.

Recently, J. A. Andersen reported that 2-(para-chlorobezamide)acetohydroxamic acid (it is commonly named "Benurestat") was used for the experimental treatment of phosphate calculus of a rat, and showed good results due to its urease inhibitory action [Refer to Investigative Urology, vol. 12, No. 5, p. 381 (1975) and U.S. Pat. No. 3,728,380]. However, it is true that, as stated more in detail later, there were seen in trace experiments in vitro the facts that said compound has strong inhibitory actions against the urease, alkalization of the urine and formation of the calculus, and low toxicity, but it will be judged that said compound has a poor usefulness as medicine, because, in the case when the compound is administered to a living body (measured six hours from the oral administration to a rat), the transfer rate into the urine is as low as 1.0%

The inventors have investigated to find out a compound having a strong urease inhibitory action, high transfer rate into the urine and low toxicity, and successfully developed the expected object by this invention.

The object of this invention is thus to provide novel hydroxamic acid derivative having urease inhibitory action.

Another object of this invention is to provide a pharmaceutical composition for the treatment of urolithiasis and pyelonephrosis containing the novel hydroxamic acid derivative.

Further object of this invention is to provide a pharmaceutical composition for the treatment of urolithiasis and pyelonephrosis having low toxicity and high transfer rate into the urine, resulting in that successive administration of the pharmaceutical composition is possible.

The compounds represented by the general formula (I) or their salts with pharmacologically acceptable bases according to this invention are superior to the above-mentioned known compound, 2-(para-chlorobenzamide)-acetohydroxamic acid for the treatment of urolithiasis, as shown in the following pharmacological experiments.

Pharmacological examination

Compounds for examination

The following examination compounds are elected, among the known compound and the compounds according to this invention.

2-(para-chloro-benzamide)-acetohydroxamic acid
(hereinafter referred to the control compound I)
2-(para-methoxy-benzamide)-acetohydroxamic acid
(hereinafter referred to the Compound A)
2-(meta-methoxy-benzamide)-acetohydroxamic acid
(hereinafter referred to the Compound B)
2-(meta-acetylaminobenzamide)-acetohydroxamic acid
(hereinafter referred to the Compound M)
2-(2-furoilamino)-acetohydroxamic acid
(hereinafter referred to the Compound R)
Item for the examination
(I) Determination of the urease inhibitory action and the transfer rate into the urine Method for the test (i) Determination of the urease inhibitory action Urease was collected and purified from sword beans (*Canavalia gladiata*) and mol concentrations of the examination compounds for inhibiting 50% of the activity of the urease were measured by the method of Kobashi et al [Refer to Biochim. Biophys. acta 227, 429–441 (1971)].

(ii) Determination of the transfer rate into the urine

Transfer rates into the urine of the examination compounds were determined according to the method of Kobashi et al [Refer to Biochemistry (Japan) vol. 44, No. 5, pp. 187–204 (1972) and Yakugaku Zasshi vol. 12, pp. 1564–1572 (1973) ] by using the male rats of SD strain having the body weight of about 280 g, administering orally each 100 mg/Kg of the compounds, and measuring the urease inhibitory action in the excreted urine within a specified period of time.

(iii) Calculation of the index

The index was calculated from the resulting values of the above examinations (i) and (ii) according to the following equation:

$$\text{Index} = \frac{\text{Transfer rate in the urine (\%)}}{I_{50} \times 10^n}$$

wherein $n$ is chosen appropriately depending on the value of $I_{50}$.

The value of the index is referred to as a standard of the urease inhibitory power of the administered examination compound in the urine.

It is seen that the larger the value of the index is, the more effectively the examination compounds transfer into the urine with a form having the urease inhibitory action. Results of the determination The urease inhibitory action and the transfer into the urine with the active form were shown in the respective examination compounds. The results are shown in the following Table 2:

Table 2

| Examination group (5 examples for each group) | 50% inhibitory concentration (M) of urease $<I_{50}>$ | Transfer rate into the urine (%) (mean value ± S. E.) Hours | | Index* |
|---|---|---|---|---|
| | | 0 – 6 | 6 – 24 | |
| Control compound I | $1.0 \times 10^{-6}$ | 1.00 | 0.50 | 1.00 |
| Compound A | $1.7 \times 10^{-6}$ | 12.00 | 0.83 | 7.06 |
| Compound B | $1.2 \times 10^{-6}$ | 12.30 | 1.50 | 10.30 |
| Compound M | $2.0 \times 10^{-6}$ | 15.0 | 0.6 | 7.5 |
| Compound R | $1.3 \times 10^{-6}$ | 15.5 | 0.68 | 11.9 |

*The transfer rate into the urine used for the calculation of the index is a mean value of the transfer rates into the urine of each animal used, during 6 hours after administration of the examination compound. Calculation was carried out with n = 6.

As it is clear from the Table 2, all examination compounds have strong urease inhibitory actions. However, the transfer rates into the urine of the respective compounds A, B, M and R are all greater than that of the control compound I. From this results, it is judged that the compounds A, B, M and R are also superior to the control compound in estimation of the index (effect index). More particularly, Indices of the compounds A, B, M and R are 4.2, 6.2, 7.5 and 11.9 respectively, while index of the control compound I is 1.0, as shown in Table 2.

(II) Determination of alkalization of the urine and the arrestment action to the calculus formation Method for determination Solutions to be examined were prepared by collecting each 18 ml of fresh urine from a normal human, and adding the respective examination compounds to each of the urine to make their concentration of $10^{-3}$M in one group, and of $2 \times 10^{-4}$ in the other group. On the other hand, same solutions containing no examination compounds were prepared as blanks.

*Proteus mirabilis* OM-1, a urease-producing bacterium, was inoculated in said solutions, so that the number of the bacteria may amount to $10^6$ cell/ml, and cultured at 37° C. After 0.8 and 24 hours of the culture time, pH values of the solutions and amounts by weight of the formed and deposited calculus were measured. The arrestment ratio of calculus formation was calculated from said values.

Results of the measurement

The following Table 3 shows results of the determination of the arrestment action to the alkalization of the urine by the examination compounds.

Table 3

| Arrestment action to alkalization of the urine | | | | |
|---|---|---|---|---|
| Examination group (5 examples for each group) | Concentration of the compound | pH value (mean value ± S. E.) Time (hour) from administration | | |
| | | 0 | 8 | 24 |
| No addition | — | 6.43±0.01 | 8.80±0.00 | 9.00±0.00 |
| Control Compound I | $10^{-3}$M | 6.75±0.003 | 6.64±0.02 | 7.03±0.01 |
| | $2\times10^{-4}$M | 6.79±0.01 | 7.30±0.00 | 8.51±0.01 |
| Compound A | $10^{-3}$M | 6.40±0.00 | 5.40±0.003 | 5.58±0.05 |
| | $2\times10^{-4}$M | 6.45±0.00 | 6.56±0.02 | 8.38±0.02 |
| Compound B | $10^{-3}$M | 6.47±0.01 | 5.41±0.01 | 6.52±0.003 |
| | $2\times10^{-4}$M | 6.45±0.01 | 6.84±0.02 | 8.71±0.01 |
| Compound M | $10^{-3}$M | 6.78±0.02 | 6.79±0.01 | 7.08±0.03 |
| | $2\times10^{-4}$M | 6.79±0.01 | 7.96±0.01 | 8.70±0.00 |
| Compound R | $10^{-3}$M | 6.46±0.00 | 5.42±0.01 | 6.98±0.02 |
| | $2\times10^{-4}$M | 6.44±0.01 | 6.65±0.02 | 8.52±0.01 |

The following Table 4 shows results of measurement of the arrestment action to the calculus formation in the urine.

Table 4

| Arrestment action to the calculus formation in the urine | | | |
|---|---|---|---|
| Examination group (5 examples for each group) | Concentration of the compound | Arrest ratio to calculus formation (%)* (mean value ± S. E.) time (hour) from administration | |
| | | 8 | 24 |
| Control compound I | $10^{-3}$M | 69.7±9.0 | 82.5±8.5 |
| | $2\times10^{-4}$M | 77.2±9.1 | 30.6±13.9 |
| Compound A | $10^{-3}$M | 96.2±0.4 | 76.6±6.0 |
| | $2\times10^{-4}$M | 99.0±1.0 | 32.0±3.4 |
| Compound B | $10^{-3}$M | 82.0±9.2 | 79.1±8.2 |
| | $2\times10^{-4}$M | 87.5±1.6 | 26.2±5.7 |
| Compound M | $10^{-3}$M | 91.5±5.1 | 81.4±5.6 |
| | $2\times10^{-4}$M | 80.1±6.7 | 38.8±8.0 |
| Compound R | $10^{-3}$M | 84.1±5.5 | 72.3±8.3 |
| | $2\times10^{-4}$M | 85.6±4.7 | 28.4±5.1 |

Arrest ratio to calculus formation (%)* = $\dfrac{\text{Weight of calculus formed in the group containing no examination compound} - \text{Weight of the calculus formed in the group containing examination compounds}}{\text{weight of the calculus formed in the group containing no examination compound}} \times 100$ As it is obvious in the Tables 3 and 4, compounds A, B, M and R arrested the alkalization of the urine and the calculus formation in the urine due to *Proteus mirabilis* OM-1 inoculated to the urine of a normal human. This action was equal to, or is rather somewhat strong, as compared with that of the control compound.

(III) Examination of acute toxicity ($LD_{50}$)

Method for examination

The examination was achieved by orally administering the examination compounds into male rats of SD strain weighing about 230 g, respectively.

Results of the measurement

The results of the measurement of the acute toxicity ($LD_{50}$) are shown in the following Table 5.

Table 5

| Results of the measurement of the acute toxicity ($LD_{50}$) | |
|---|---|
| Examination group (10 examples for each group) | $LD_{50}$ mg/Kg |
| Control compound 1 | >5,000 |
| Compound A | >5,000 |
| Compound B | >5,000 |
| Compound M | >5,000 |
| Compound R | >5,000 |

As it is obvious from the Table 5, it was affirmed that the acute toxicities ($LD_{50}$) of the compounds A, B, M and R are as low as that of the control compound.

(IV) Remarks on the observation of the acute toxicity (1) Remarks on the observation of the general conditions and remarks on the dissection Method for examination:

Eight week-old rats of SD strain (body weight: about 230 g for male and about 160 g for female) were used as the subject animals. The examination compounds were forcedly and orally administered in the following dosages, wherein 14 rats (7 male rats and 7 female rats, respectively) were used.

| Compounds A and B : | 5,000 mg/Kg, | 4,000 mg/Kg, | 2,000 mg/Kg |
|---|---|---|---|
| Control Compound I : | 5,000 mg/Kg, | 3,000 mg/Kg, | 1,800 mg/Kg |
| | 1,080 mg/Kg, | 648 mg/Kg | |

Results of the observation (i) Table 6 shows remarks on the observation of the general conditions.

Table 6

| Remarks on the observation of the general conditions | | | |
|---|---|---|---|
| Item of the observation | Compound A | Compound B | Control Compound I |
| Behavior | No change was observed in all administration groups | Some extent of decrease of voluntary motions was observed in administration groups of dosage of 4,000 mg/Kg and of 5,000 mg/Kg. | Decrease of voluntary motions was observed in all administration groups of male, and in the administration groups of female of dosage of 3,000 mg/Kg and of 5,000 mg/Kg. |
| Symptom | No change was observed in all administration groups | Hair raising was observed in the administration groups of 4,000 mg/Kg and of 5,000 mg/Kg. | Marantic change accompanying with dishevelled hair was observed in all administration groups of male, and in the administration groups |

Table 6-continued

| Item of the observation | Remarks on the observation of the general conditions | | |
|---|---|---|---|
| | Compound A | Compound B | Control Compound I |
| Body weight | Smoothly increased in all administration groups | Smoothly increased in all administration groups | of female of dosage of 3,000 mg/Kg and of 5,000 mg/Kg. 10% decrease on average was observed in all administration groups |
| Baited amount | No change was observed in all administration groups | No change was observed in all administration groups | Decrease in baited amount was observed in all administration groups |
| Number of death examples* | Male 1/7 Female 0/7 | Male 1/7 Female 3/7 | Male 3/7 Female 0/7 |

*In all cases, death examples were observed only in the administration group of dosage of 5,000 mg/Kg ($LD_{50}$ was more than 5,000 mg/Kg in any case).

(ii) Remarks on the dissection

The dissection was performed, for the death examples, at the time of death and, for the survivor example, after killing by discharging the blood when the observation of the general conditions was finished. The organs in the thoracic cavity and the abdominal cavity were closely observed with a macroscopic manner. The results are shown in the following Table 7.

Table 7

| | Remarks on the dissection | |
|---|---|---|
| | Survivor example | Death examples |
| Compound A | No abnormality was observed in thoracic cavity and abdominal cavity in all administration groups | Erosion was observed in ventriculus or pars cranialis of duodenum |
| Compound B | No abnormality was observed in thoracic cavity and abdominal cavity in all administration groups | Erosion was observed in ventriculus or pars cranialis of duodenum |
| Control Compound I | Blacking change and hypertropy of spleen were observed in all administration groups of male, and in the administration groups of female of dosage of more than 1080 mg/Kg. These degrees depended on the dosage. | Petechiae and ulcer were observed in ventriculus and dropsy in pars cranialis of duodenum. |

(2) Remarks on examination of urine

Method for examination:

To 5 male SD strain rats having the body weight of about 280 g in the respective groups, the examination compounds were forcedly and orally administered in a ratio of 100 mg/Kg in each time.

Natural urinations were respectively recovered 6 hours and 6 – 24 hours from the administration. As for control group wherein no examination compound is administered, natural urination was similarly recovered. Amount and pH value of the recovered urine were measured. Further, qualitative reaction concerning the respective items of protein, glucose, ketone substances, and occult blood in the urine was carried out by using Labstix text paper (manufactured and sold by Ames Company). Judgement was ranked as five levels, that is, (−), (±), (+), (++) and (+++).

Results of Examination

Table 8 shows remarks on examination of urine.

Table 8

| Examination Item | Remarks on Examination of urine | | | | | | | |
|---|---|---|---|---|---|---|---|---|
| | Protein | | Glucose | | Ketone substances | | Occult blood | |
| Examination Groups (Respective 5 groups) | hours | | hours | | hours | | hours | |
| | 0–6 | 6–24 | 0–6 | 6–24 | 0–6 | 6–24 | 0–6 | 6–24 |
| No Examination compound is used | + | ± | − | − | − | − | − | − |
| Compound A | + | ± | − | − | − | − | − | − |
| Compound B | + | ± | − | − | − | − | − | − |
| Control Compound I | ++ | +++ | +++ | +++ | ++ | +++ | − | − |

As for amount and pH value of the urine, there was not found the difference between the Compounds A, B and Control Compound I, as compared with the group wherein no examination compound is administered.

As clear from the data of the Table 8, there was not found the difference between the Compounds A and B, as compared with the group wherein no examination compound is administered, with respect to the items of protein, glucose, ketone substances and occult blood. On the contrary, the Control Compound I shows a strong positive reaction with respect to the items of protein, glucose and ketone substances, and it was observed that toxicity is strong.

From the summarized remarks on the data of the Tables 6, 7 and 8, it is judged that safety of the Compounds A and B is outstandingly good. On the contrary, it was observed that the Control Compound I brings a change in marasmus or debility accompanying with the decrease in the body weight. Even in the cases of survivors, it is judged that toxicity is strong, from the facts that there was observed a change in black and hypertrophy of the spleen, and the outstanding positive reaction was shown in the items of protein, glucose and ketone substances according to the remarks on the examination of the urine.

In viewpoint of the results of the above pharmacological examinations, the compounds of the general formula (I) typified by the compounds A, B, M and R are judged to have a great value as medicine for the treatment of the urolithiasis, since these compounds have strong urease inhibitory action, arrestment action to the calculus formation based on said urease inhibitory action, large transfer rate into the urine such as about 10 – 15 times of that of the control compound I, and high safety. Further, it is clinically said that the pyelonephrosis caused by the infection of a urease-producing bacterium such as *Bacillus proteus* takes a serious turn due to the toxicity of ammonia produced by decomposition of urea in the urine, but it is also expected that the compounds of the general formula (I) are used for the treatment of such pyelonephrosis.

The compounds of the general formula (I) can be administered orally or by injection. Administration amount for the treatment of an adult patient varies from 25 to 3,000 mg a day, and preferably 1,500 mg a day, for example.

The compounds of the general formula (I) are expected to have a superior effect for the treatment of the urolithiasis in a form of single use and they are also expected to have much more effect by using them together with other anti-bacilluses such as Ampicillin, sulfamethoxazole, nitrofurantoin, and the like.

The compounds of the general formula (I) can be produced in a type or form of administration by any conventional processes for the preparation. Accordingly, this invention includes also pharmaceutical compositions suitable for a medicament for human body, which contain at least one of the compounds of the general formula (I). Such compositions are provided for use with any required pharmaceutical carrier or excipient by a conventional method.

These compositions are preferably provided in a suitable form for assimilation or absorption in the digestive system. Tablet and capsule for oral administration are in an administration form of unit amount, and may contain any conventional excepients such as binders e.g. syrup, gum arabic, gelatin, sorbit, tragacant gum and polyvinyl pyrolidone; constituents e.g. milk sugar, corn starch, calcium phosphate, sorbit and glycine; lubricants e.g. magnesium stearate, talc, polyethylene glycol and silica; disintegrater e.g. potato starch; or acceptable wetting agents e.g. sodium lauryl sulphate. The tablet may be coated by a well known method in this art. Liquid preparation for oral administration may be an aqueous or oily suspension, a solution, a syrup, elixir or the like, or may be a dried products which can be re-dissolved in water or other suitable vehicles prior to use. Such liquid preparation may contain conventional additives such as suspension agents e.g. sorbit syrup, methyl cellulose, glucose/sugar syrup, gelatin, hydroxy ethyl cellulose, carboxy methyl cellulose, aluminium stearate gel, and hydrogenated edible oil; emulsifiers e.g. lecitin, monooleyl sorbitane and gum arabic; non-aqueous vehicles, e.g. almound oil, fractionated coconut oil, oily ester, propylene glycol and ethyl alcohol; antiseptics, e.g. methyl-p-hydroxy benzoate, propyl p-hydroxy benzoate and sorbic acid.

The compositions for injection are provided in a form of ampoule for amount of unit administration, or in a form of container for a large amount of administration with antiseptics. These compositions may be in a form of suspension, solution, or emulsion in an aqueous or oily vehicle, and may contain a treatment agent such as a suspension agent, a stabilizer and/or dispersion agent. On the other hand, the active components may be in a powdery form which can be re-dissolved, prior to use, in an appropriate vehicle, such for example, as sterilized water free from exothermic substances.

This invention will be illustrated by the following examples concerning processes for synthesis of the compounds of the general formula (I) and formulations containing such compounds.

Synthesis example 1

Synthesis of 2-(para-methoxy benzamide)-acetohydroxamic acid

A solution comprising 112 g (2.0 mols) of potassium hydroxide in 500 ml of methanol was added to a solution comprising 69.5 g (1.0 mol) of hydroxylamine hydrochloride in 500 ml of methanol. Inorganic salts formed were filtered off. To the filtrate, 142.4 g (0.6 mols) of ethyl ester of p-methoxy hippuric acid were added. The mixture was sirred for one hour at a room temperature and allowed to stand overnight. The reaction solution was distilled at 60° C. under reduced pressure to remove the solvent. The residue was dissolved in 500 ml of water. Acetic acid was added to the residue under cooling to make it pH 5.0. Crystalline masses formed were recovered by filtration and recrystallized from ethanol. There were thus obtained 113.8 g of the object material which exhibits the melting point of 161.0°–161.5° C. The yield was 84.6%.

Elementary analysis of the product for $C_{10}H_{12}N_2O_4$ gives:

|  | C | H | N |
|---|---|---|---|
| Calculated (%) | 53.57 | 5.39 | 12.50 |
| Found (%) | 53.56 | 5.39 | 12.61 |

Synthesis example 2

Synthesis of 2-(meta-methoxybenzamide)-acetohydroxamic acid

A solution containing 80 g (2 mols) of sodium hydroxide in 400 ml of methanol was added to a solution containing 83.4 g (1.2 mols) of hydroxylamine hydrochloride in 800 ml of methanol. Inorganic salts formed were filtered off. To the filtrate, 180 g (0.73 mols) of ethyl ester of meta-methoxy hippuric acid were added. The mixture was stirred for one hour at a room temperature and allowed to stand overnight. The reaction solution was heated to 60° C. and the solvent was distilled off under reduced pressure. The residue was dissolved in 500 ml of water, and acetic acid was added to said solution under cooling, so that pH of the solution may reach to 5.0, then the resulting crystals were removed by filtration.

The crystals were recrystallized from iso-propanol. 121.9 g of the object were thus obtained, which has the melting point of 132.0°–132.5° C. The yield was 74.5%.

Elementary analysis for the product for $C_{10}H_{12}N_2O_4$ gives:

|  | C | H | N |
|---|---|---|---|
| Calculated (%) | 53.57 | 5.39 | 12.50 |
| Found (%) | 53.53 | 5.42 | 12.70 |

Synthesis example 3

Synthesis of 2-(meta-acetylaminobenzamide)-acetohydroxamic acid

A solution containing 52.5 g of potassium hydroxide in 200 ml of methanol was added to a solution containing 27.8 g of hydroxylamine hydrochloride in 250 ml of methanol with cooling. Inorganic salts produced were filtered off. To the filtrate, 79.3 g of ethyl metaacetylamino hippurate were added. The mixture was stirred for one hour at a room temperature, and allowed to stand overnight. The reaction solution was distilled at 60° C. under a reduced pressure to remove the solvent. The residue was dissolved in 200 ml of water. The solution was made to pH 5.0 by adding acetic acid under cooling. The crystals formed are collected by filtration and recrystallized from methanol. The object material was obtained, which has the melting point in the range from 178.0° to 179.0° C.

|  | C | H | N |
|---|---|---|---|
| Calculated (%) | 52.58 | 5.22 | 16.73 |
| Found (%) | 52.40 | 5.37 | 16.63 |

Synthesis example 4

Synthesis of 2-(para-propionylaminobenzamide)-acetohydroxamic acid

A solution containing 13.1 g of potassium hydroxide in 70 ml of methanol was to a solution containing 7.0 g of hydroxylamine hydrochloride in 50 ml of methanol. Inorganic salts formed were filterred off. To the filtrate, 12.6 g of ethylester of para-propionylamino hippuric acid were added. The mixture was stirred for one hour at a room temperature, and allowed to stand overnight. Large amounts of precipitates produced were collected by filtration and suspended in 150 ml of water. Acetic acid was added with vigorous stirring to the suspension, so that pH of the suspension may amount to 5.0. The crystals formed were collected by filtration and recrystallized from methanol. The object material was obtained, which has the melting point (decomposition point) higher than 205° C.

|  | C | H | N |
|---|---|---|---|
| Calculated (%) | 54.33 | 5.70 | 15.84 |
| Found (%) | 54.07 | 5.74 | 15.88 |

Synthesis example 5

Synthesis of 2-(2-furoilamino)-acetohydroxamic acid

A solution containing 16.4 g of potassium hydroxide in 60 ml of methanol was added to a solution containing 9.7 g of hydroxylamine hydrochloride in 60 ml of methanol with cooling. Inorganic salts produced were filterred off. To the filtrate, 19.7 g of ethyl N-(2-furuoil)-glycinate were added. The mixture was stirred for one hour at a room temperature, and allowed to stand overnight. The reaction solution was distilled at 60° C. under a reduced pressure to remove the solvent. The residue was dissolved in 100 ml of water. The solution was made to pH 5.0 by adding acetic acid under cooling. 8.5 g of cupric chloride di-hydrate were added thereto, whereby a complex of copper salt was obtained. This complex was suspended in 100 ml of methanol, and gaseous hydrogen sulfide was passed through therein. The precipitate of copper sulfide was filtered off. The filtrate was distilled at 60° C. under a reduced pressure to remove the solvent. The product was recrystallized from methanol. The object material was obtained, which has the melting point in the range from 150.0° to 151.0° C.

|  | C | H | N |
|---|---|---|---|
| Calculated (%) | 45.65 | 4.38 | 15.21 |
| Found (%) | 45.85 | 4.46 | 15.01 |

Synthesis example 6

Synthesis of 2-(2-thenoilamino)-acetohydroxamic acid

A solution containing 16.4 g of potassium hydroxide in 60 ml of methanol was added to a solution containing 9.7 g of hydroxylamine hydrochloride in 60 ml of methanol with cooling. Inorganic salt produced was filtered off. To the filtrate, 21.3 g of ethyl N-(2-thenoil)-glycinate were added. The mixture was stirred for one hour at a room temperature, and allowed to stand overnight. The reaction solution was distilled at 60° C. under a reduced pressure to remove the solvent. The residue was dissolved in 100 ml of water. The solution was made to pH 5.0 by adding acetic acid under cooling. The crystals formed were collected by filtration and recrystallized from ethanol. The object material was obtained, which has the melting point in the range from 153.0° to 153.5° C.

|  | C | H | N |
|---|---|---|---|
| Calculated (%) | 41.99 | 4.03 | 13.99 |
| Found (%) | 41.89 | 4.02 | 14.25 |

| Preparation example 1: Tablet | |
|---|---|
| 2-(para-methoxybenzamide)-acetohydroxamic acid | 10,000 mg |
| mannit | 4,000 mg |
| potato starch | 1,000 mg |
| magnesium stearate | 100 mg |

According to the above formulation, 160 tablets were prepared by conventional process. Each one of these tablets contained 100 mg of 2-(para-methoxybenzamide)-acetohydroxamic acid.

| Preparation example 2: Medicament for injection | |
|---|---|
| 2-(para-methoxybenzamide)-acetohydroxamic acid | 4.0 g |
| HCO-60 (manufactured and sold by Nikko Chemicals, in Japan) | 8.0 g |
| D-sorbit | 30.0 g |
| Potassium hydroxide, extra pure grade | appropriate amount |
| Distilled water for injection sufficient to make up the total to | 500 ml |

According to the above formulation, 100 ampoules of the medicament for injection (5 ml per ampoule) were prepared by conventional manner. These ampoules were subjected, if required, to isotonic process or hypertonic process and sterilization under high pressure. This medicament contains 40 mg of 2-(para-methoxybenzamide)-acetohydroxamic acid per ampoule.

| Preparation example 3: Tablet | |
|---|---|
| 2-(meta-acetylaminobenzamide)-acetohydroxamic acid | 10,000 mg |
| Mannit | 4,000 mg |
| Potato starch | 1,000 mg |
| Magnesium stearate | 100 mg |

According to the above formulation, 100 tablets were prepared by a conventional process. Each one of these tablets contains 100 mg of 2-(meta-acetylaminobenzamide)-acetohydroxamic acid.

| Preparation example 4: Capsule | |
|---|---|
| 2-(meta-propionylaminobenzamide)-acetohydroxamic acid | 15,000 mg |
| Corn starch | 5,000 mg |
| Talc | 20 mg |

According to the above formulation, 100 capsules were prepared by a conventional process. Each one of these capsules contains 150 mg of 2-(meta-propionylaminobenzamide)-acetohydroxamic acid.

| Preparation example 5: Tablet | |
|---|---|
| 2-(2-furoilamino)-acetohydroxamic acid | 15,000 mg |
| Milk sugar | 3,000 mg |
| Potato starch | 2,000 mg |
| Magnesium stearate | 100 mg |

According to the above formulation, 100 tablets were prepared by a conventional process. Each one of these tablets contained 150 mg of 2-(2-furoilamino)-acetohydroxamic acid.

| Preparation example 6: Suspension | |
|---|---|
| 2-(2-thenoilamino)-acetohydroxamic acid | 1.0 mg |
| Sodium carboxymethyl cellulose | 0.2 g |
| Strawberry syrup | 8.0 ml |
| Plain syrup | 16.0 ml |

According to the above formulation, wholly homogeneous suspension was prepared by a conventional process.

What is claimed is:

1. A compound having the general formula:

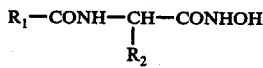

wherein $R_1$ is a substituted phenyl group represented by a formula:

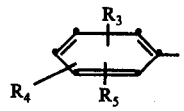

wherein $R_3$, $R_4$ and $R_5$ are selected from the group consisting of hydrogen and a lower alkoxy group, provided that at least one of them is a lower alkoxy group, $R_2$ is hydrogen or methyl group, and its salt of pharmacologically acceptable base.

2. The compound according to claim 1, wherein the compound is represented by the formula:

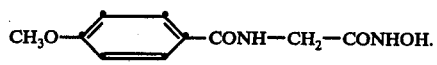

3. The compound according to claim 1, wherein the compound is represented by the formula:

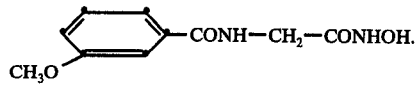

4. A medicament for urolithiasis which comprises a compound having the general formula:

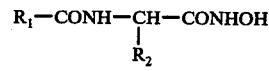

wherein $R_1$ is a substituted phenyl group represented by a formula:

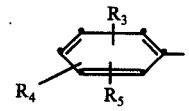

wherein $R_3$, $R_4$ and $R_5$ are selected from the group consisting of hydrogen and a lower alkoxy group, provided that at least one of them is a lower alkoxy group, $R_2$ is hydrogen or methyl group, and its salt of pharmacologically acceptable base.

5. The medicament for the treatment of urolithiasis according to claim 4, which comprises the compound of the formula:

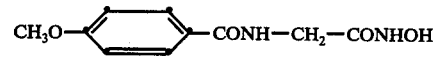

and a salt of the compound with a pharmacologically acceptable base.

6. The medicament for the treatment of urolithiasis according to claim 4, which comprises the compound of the formula:

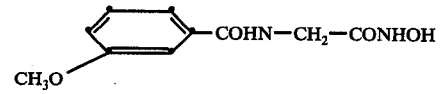

and a salt of the compound with a pharmacologically acceptable base.

7. A medicament for the pyelonephrosis which comprises a compound having the general formula:

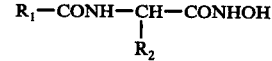

wherein $R_1$ is a substituted phenyl group represented by a formula:

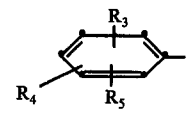

wherein $R_3$, $R_4$ and $R_5$ are selected from the group consisting of hydrogen and a lower alkoxy group, provided that at least one of them is a lower alkoxy group, $R_2$ is hydrogen or methyl group, and its salt of pharmacologically acceptable base.

* * * * *